United States Patent

Pöchlauer et al.

Patent Number: 5,412,110
Date of Patent: May 2, 1995

[54] ENZYMATIC PROCESS TO SEPARATE RACEMIC MIXTURES OF DELTA VALEROLACTONES

[75] Inventors: Peter Pöchlauer, Linz; Marion Wagner, Katsdorf, both of Austria

[73] Assignee: Chemie Linz Gesellschaft m.b.H., Linz, Austria

[21] Appl. No.: 936,782

[22] Filed: Aug. 28, 1992

[30] Foreign Application Priority Data

Jul. 6, 1992 [AT] Austria ................... 1374/92

[51] Int. Cl.⁶ ................... C07D 304/30; C07D 305/12
[52] U.S. Cl. .................... 549/291; 549/292; 549/328
[58] Field of Search ............ 549/291, 292, 328

[56] References Cited

U.S. PATENT DOCUMENTS 4,963,492 10/1990 Keller et al. ................. 435/155
5,084,392 1/1992 Miyazawa et al. ............. 549/292

FOREIGN PATENT DOCUMENTS 0269453 6/1988 European Pat. Off.
0439779 8/1991 European Pat. Off.
91/1153 2/1991 South Africa.

OTHER PUBLICATIONS

Laymen et al, J. Chem. Soc., Chem. Commun. (1988), pp. 1459–1461.

*Primary Examiner*—C. Warren Ivy
*Assistant Examiner*—Raymond Covington
*Attorney, Agent, or Firm*—Wenderoth, Lind & Ponack

[57] ABSTRACT

Process to separate racemic mixtures of beta-hydroxy or beta-acyloxy-delta-valerolactones, which in position 2 and/or 5 of the lactone ring are substituted by hydrogen, alkyl groups having 4 to 20 C atoms, which are optionally penetrated by an oxygen atom, or by aralkyl groups, whereby not both positions are substituted by hydrogen, through reaction of the racemic mixture in the presence of a hydrolase with or without esterifying agent in a diluent and separation of the reaction mixture, which contains an enantiomerically pure beta-hydroxy-delta-valerolactone and an enantiomerically pure beta-acyloxy-delta-valerolactone, through conventional methods into the enantiomically pure compounds, a process for the manufacture of enantiomerically pure oxetanones using said separation process and enantiomerically pure beta-acyloxy-delta-valerolactones.

11 Claims, No Drawings

ENZYMATIC PROCESS TO SEPARATE RACEMIC MIXTURES OF DELTA VALEROLACTONES

It is described in the ZA 91/1153 that in particular specific enantiomers of oxetanones, which are substituted by alkyl chains or aryl groups, exhibit good pharmaceutical actions.

In the ZA 91/1153 two reaction sequences are described for the manufacture of these enantiomerically pure oxetanones.

According to reaction sequence 1, starting from methyl acetoacetate, a racemic mixture of a (2RS,3RS,5SR)-2-hexyl-3-hydroxy-5-undecyl-delta-valerolactone is produced as the intermediate product, which is converted by means of several steps into race-(2RS,3RS,5SR)-5-benzyloxy-2-hexyl-3-hydroxyhexadecanoic acid. In this step the resolution of racemates takes place through the formation of a salt with the aid of an enantiomerically pure amine, thus separating the (2S,3S,5R) enantiomer from the (2R,3R,5S)-enantiomer. Subsequently the enantiomerically pure (2S,3S,5R) compound is cycled into the enantically pure oxetanone. Since in this reaction sequence the resolution of racemates occurs very late, the enantiomer which is useless for the manufacture of enantiomerically pure oxetanones, must also be converted by way of several steps, before it is finally rejected.

According to reaction sequence 2, enantiomerically pure 3-hydroxytetradecanoic acid ester is converted by way of several steps into enantiomerically pure 5-((R)-3-benzyloxy-1-hydeoxytetradecylidene)-2,2-dimethyl-m-dioxan-4,6-dione, which is cycled without any racemation into (R)-5,6-dihydro-6-undecyl-2H-pyran-2,4(3H)-dione, and is left to react further of several steps into enantiomerically pure oxetanohe. In so doing, however, enantiomerically pure 3-hydroxytetradecanoic acid ester, which is not simple to prepare, must be used as the starting product. Since the above described cyclization into pyran proceeds with very poor yields, large quantities of the enantiomerically pure material are lost during this reaction sequence.

It has now been found that to prepare enantiomerically pure oxetanones according to the ZA 91/1153 the resolution of racemates can be conducted very simply and effectively in an early process step of the reaction sequence 1, whereby the above described cyclization into pyran is avoided.

If a racemic mixture of beta-hydroxy-delta-valerolactones or of beta-acyloxy-delta-valerolactones, as described above, is esterified or hydrolyzed selectively by using a hydrolase, one obtains in a simple manner a mixture of an enantiomerically pure (2S,3S,5R)-beta-hydroxy-delta-valerolactone with an enantiomerically pure (2R,3R,5S)-beta-acyloxy-delta-valerolactone or a mixture of an enantiomerically pure (2R,3R,5S)-beta-hydroxy-delta-valerolactone with an enantiomerically pure (2S,3S,5R)-beta-acyloxy-delta-valerolactone, which can be separated then in a very simple manner. Thereby the reaction comes surprisingly completely roan end after conversion of one of the enantiomers, so that products of highest purity are obtained. The desired enantiomerically pure oxetanones can be obtained, according to the method described in the ZA 91/1153 from the separated compounds, if necessary after splitting off of the acyl group.

The enzymatic reaction is completed in an extremely short period of time. This was totally unexpected, because it is described in the EP-A-0 439 779 that the enzymatic separation of alpha or beta-hydroxy-delta-valerolactones, which are unsubstituted or substituted by methyl groups in the lactone ring, takes up to 150 hours with the aid of esterification of the hydroxy group with a lipase and a vinyl ester. In contrast, the reaction according to the invention is generally completed within a few hours, in some cases even within 1 to 2 hours, even though the beta-hydroxy-valerolactones, according to the invention, are substituted by alkyl chains or aryl groups, so that the reaction should run even much slower for steric reasons than that described in the EP-A-0 439 779.

Therefore, the object of the invention is a process to separate racemic mixtures of a compound of the general formula

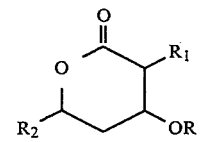

I in which R denotes hydrogen or an acyl group, and $R_1$ and $R_2$ denote independently of each other hydrogen, a straight chained or branched alkyl group having 4 to 20 C atoms, which can be penetrated by an oxygen atom in a position other than the alpha or beta position or denote an unsubstituted aralkyl group or an aralkyl group substituted by inert groups under the reaction conditions, provided that $R_1$ and $R_2$ do not denote simultaneously hydrogen, which is characterized by the fact that the racemic mixture of a compound of the general formula I is introduced in a diluent and in the presence of a hydrolase and, in the case that R in the general formula I denotes hydrogen in the presence of an esterifying agent, is left to react, whereby a reaction mixture is produced that contains an enantiomerically pure beta-hydroxy-delta-valerolactone and an enantiomerically pure beta-acyloxy-delta-valerolactone, which is separated by the conventional method.

By racemic mixture of general formula I are understood not only mixtures, which contain the enantiomer in a ratio of 1:1, but also mixtures, which contain the enantiomers in any arbitrary composition, in which, therefore, one of the enantiomers is enriched.

In the general formula I R denotes hydrogen or an acyl group, preferably hydrogen. An acyl group is a group of the general formula —CO—$_3$, in which $R_3$ denotes an unsubstituted or by groups which are inert under the reaction conditions substituted alkyl or aryl group, preferably an unsubstituted alkyl group having 1 to 6 C atoms, quite preferably having 1 to 4 C atoms. $R_1$ and $R_2$ denote independently of each other hydrogen, where $R_1$ and $R_2$ do not denote simultaneously hydrogen; an alkyl group having 4 to 20, preferably having 4 to 17 C atoms, which is straight chained or branched, preferably however straight chained; an alkyl group having 4 to 20, preferably having 4 to 17 C atoms, which is straight chained or branched and which is penetrated by an oxygen atom in a position other than the alpha or beta position; or an unsubstituted aralkyl group or an aralkyl group substituted by alkyl or alkoxy groups, where the alkyl or alkoxy groups exhibit preferably 1 to 6 C atoms. Preferably there is one benzyl group as the aralkyl group. Preferably $R_1$ and $R_2$ denote independently of each other hydrogen or alkyl groups, in particular $R_1$ and $R_2$ denote preferably alkyl groups.

An especially preferred beta-hydroxy-delta-valerolactone is one of the general formula I, in which R denotes hydrogen or an acyl group; $R_1$ denotes an alkyl group having 4 to 17 C atoms and $R_2$ denotes an alkyl group having 6 to 17 C atoms.

The racemic mixtures of a compound of the general formula I, in which R denotes hydrogen, can be prepared according to one of the methods disclosed in the ZA 91/1153. Racemic mixtures of a compound, in which R denotes an acyl group, can be prepared by any esterification method, by means of which the R group can be introduced, from the racemic mixture of the compounds of the general formula I, in which R denotes hydrogen. Preferably the esterification is effected by converting a racemic mixture of a compound of the general formula I, in which R denotes hydrogen, with a carboxylic acid anhydride or carboxylic acid chloride in the presence of bases such as pyridine, triethylamine, dimethylaminopyridine.

To carry out the process according to the invention, a racemic mixture of a compound of the general formula I is introduced into a diluting agent. If R denotes an acyl group, no esterifying agent is added. In this case water or an aqueous salt or buffer solution, preferably a phosphate buffer, which exhibits a pH value that is optimal for the esterase used, is used as the diluent. The buffer solution can be added as such or together with organic diluents. Suitable organic diluents are, for example, aliphatic or aromatic hydrocarbons such as hexane, toluene, xylenes, ethers such as diethyl ether, diisopropyl ether, tert.-butyl-methyl-ether, tetrahydrofuran, ketones such as acetone, butanone, tert.-butyl-methyl-ketone or mixtures of such diluents. Through the addition of the organic diluent to the buffer solution, a partial solution or dissolution of the starting racemic mixture is achieved. If the organic diluent is not miscible with water, the process of the invention proceeds as a 2 phase reaction, so that in this case good thorough mixing of the phases is provided.

If R denotes hydrogen, an esterifying agent is added to the starting racemic mixture. Conventional esterifying agents such as carboxylic acid esters, for example compounds of the general formula $R_5COOR_6$, in which $R_5$ and $R_6$ denote independently of each other alkyl, aryl or aralkyl groups, carboxylic acid ester of multivalent alcohols, for example glycerol triacylates such as glycerol triacetate, glycerol tributyrate, carboxylic acid anhydrides, as disclosed, for example, in the EP-A-0 269 453, or vinyl esters, for example, according to the U.S. Pat No. 4,963,492, can be used as esterifying agents. Preferably a carboxylic acid ester of the general formula $R_5COOR_6$, in which $R_5$ and $R_6$ denote independently of each other an alkyl group having 1 to 6 C atoms; a glycerol triacylate; a vinyl ester of the general formula $CH_2=CH-O-CO-R_7$, in which $R_7$ denotes hydrogen, an alkyl group having 1 to 18 C atoms or a phenyl group, especially preferred an alkyl group having 1 to 6 C atoms; a carboxylic acid anhydride of the general formula $R_8-CO-O-CO-R_9$, in which $R_8$ and $R_9$ are the same or not the same, preferably the same and denote an alkyl, aryl or aralkyl group, especially preferred an alkyl group having 1 to 6 C atoms, is added as the esterifying agent. In particular, acetic anhydride, propionic acid anhydride, vinyl acetate, ethyl acetate, glycerol triacetate or glycerol tributyrate are added preferably as the esterifying agent.

In this case suitable diluents are inert diluents, for example aliphatic or aromatic hydrocarbons such as hexane, toluene, xylene, ethers such as diethyl ether, diisopropyl ether, tert.-butyl-methyl-ether, ketones such as tert.-butyl-methyl-ketone, also the esterifying agent itself or mixtures of the aforementioned diluents.

At least one half equivalent, preferably 1 to 8 equivalents of the esterifying agent, is added per equivalent of the racemic mixture with the general formula I, in which R denotes hydrogen. In general better results are obtained with an excess of the esterifying agent. In particular the esterifying agent is also added preferably simultaneously as the diluent, whereby a very high excess of the esterifying agent is added.

If a carboxylic acid anhydride is added as the esterifying agent, a base, for example potassium or sodium hydrogen carbonate, is added to the reaction mixture in order to bond the resulting acid.

The solution or suspension of the starting racemic mixture is then brought into contact with a hydrolase. By hydrolases are understood, e.g. lipases, esterases, proteases. Preferred are lipases, especially preferred lipases of the microorganisms Alcaligenes, Pseudomonas, Candida, Mucor. The hydrolase can be added as cleaned enzyme fractions or as a suspension of microorganisms, which contains the hydrolase, but is added preferably as a cleaned enzyme fraction. The hydrolase can be added as such or immobilized; that means, physically or chemically bonded to a carrier.

Hydrolases can be bought and with respect to the reaction conditions are added advantageously according to the instructions of the seller.

During the conversion according to the invention the hydrolase suffers virtually no noteworthy loss in activity and can, therefore, be added repeatedly.

The suitable quantity of hydrolase depends on the chemical nature of the starting compound used, the hydrolase used, the diluent used and the optional esterifying agent and can be readily determined by pilot tests. Since the added hydrolase is reusable, a large quantity of hydrolase can be added without harm in those cases in which a large quantity of hydrolase has a good effect on the reaction speed, without rendering the process costs notably expensive. Preferably about 0.05 to 2 g of hydrolase are added per gram of starting compound of the general formula I.

Since hydrolases can both link and break ester bonds, they can carry out both the selective hydrolysis of the compounds of the general formula I, in which R denotes an acyl group and the selective esterification of the compounds of the general formula I, in which R denotes hydrogen.

Either the hydrolase is added to the reaction mixture, or the reaction mixture is pumped over the hydrolase. As the reaction temperature preferably that temperature is selected at which the hydrolase shows its highest activity. This temperature is generally noted for commercially available hydrolases and can otherwise be readily determined by simple pilot tests. The reaction temperature ranges from $-10°$ C. to the deactivation temperature of the added hydrolase, depending on the hydrolase used and depending on the substrate used. Generally the reaction temperature ranges from room temperature to 60° C.

Contacting the hydrolase with the racemic mixture of the compound of the formula I, the hydrolase produces a reaction mixture containing an enantiomerically pure beta-hydroxy-delta-valerolactoae and an enantiomerically pure beta-acyloxy-delta-valerolactone. Particulary using a vinyl ester as the esterifying agent, the reaction is finished totally unexpected in a very short period of time. The reaction proceeds with virtually 100% selectivity, since it has been found that the reaction comes to an end by itself after conversion of one of the enantiomers.

Therefore, the conversion can be followed by simple thin layer or gas chromatography and it is not necessary, as in the case of less selective reactions, to break off the reaction at a specific degree of conversion, in order to prevent overreaction and contamination of the desired product. Since enzymes exhibit only very rarely such a high selectivity and since it is known in particular of lipases that they prefer one enantiomer during conversions, but that they also generally convert the second enantiomer, as soon as the substrate is impoverished of the preferred enantiomer, the high selectivity of the reaction of the invention is extremely surprising.

The desired enantiomer is subsequently separated from the reaction mixture. Since the one enantiomer in the reaction mixture is a compound with a free and the second enantiomer is a compound with an acylated hydroxy group, the separation is very simple to perform and can be conducted by known methods such as crystallization, extraction, distillation, chromatography.

It has turned out to be especially surprising in the case of compounds, in which R denotes a hexyl and $R_2$ denotes an undecyl group, that the mixture of enantiomerically pure hydroxyl and acyloxy compounds can be separated through crystallization, whereby the compound with the free hydroxy group predominantly crystallizes out, whereas the compound with the acylated hydroxy group remains predominantly in solution. Through filtering off the crystallizate the enantiomerically pure acetoxy compound is obtained in the mother liquor.

Enantiomerically pure compounds of the general formula I, in which R denotes an acyl group and in which $R_1$ and $R_2$ have the aforementioned meaning are, with the exception of (2S,3S,5R)-2-hexyl-3-benzoyloxy-5-undecyl-delta-valerolactone, which is described in the ZA 91/1153, are new and also object of the invention.

The separated compounds can be subsequently purified still further by conventional methods such as crystallization, recrystallization, chromatography.

In a preferred embodiment of the invention, a racemic mixture of a compound of the general formula I, in which $R_1$ and $R_2$ denote alkyl groups having 4 to 20 C atoms and R denotes an acyl group, is suspended in a sodium phosphate buffer at pH 7 with the addition of an organic diluent. The reaction mixture is brought into contact with a lipase at temperatures ranging from room temperature to 60° C., whereby either the lipase is added to the reaction mixture, or the reaction mixture is pumped continuously over a lipase, which is insoluble in the reaction, preferably over an immobilized lipase.

The pH value of the reaction mixture is held constant through the addition of an aqueous base. The course of the reaction is followed by means of chromatography or with the aid of the quantity of the consumed base. The mixture that is obtained and contains a virtually enantiomerically pure beta-hydroxy-delta-valerolactone and a virtually enantiomerically pure beta-acyloxy-delta-valerolactone is separated by simply cooling the reaction mixture, whereby the hydroxy compound precipitates as crystals, whereas the acyloxy compound remains in solution.

In another preferred embodiment of the invention, a racemic mixture of a compound of the general formula I, in which R denotes hydrogen and $R_1$ and $R_2$ denote alkyl groups having 4 to 20 C atoms, is dissolved or suspended in a carboxylic acid ester of the general formula $R_5COOR_6$, a vinyl alkanoate of the general formula $CH_2=CH-O-COR_7$ or a carboxyl acid anhydride of the general formula $R_8-CO-O-CO-R_9$, in which $R_5$, $R_6$, $R_7$, $R_8$ and $R_9$ denote an alkyl group having 1 to 6 C atoms, or in a glycerol triacylate, especially preferred in glycerol triacetate, glycerol tributyrate, vinyl acetate, acetic anhydride, propionic acid anhydride or ethyl acetate, if desired with the use of an inert diluent. If a carboxylic acid anhydride is used, a base, for example potassiumhydrogen carbonate, is added, in order to maintain the pH value of the reaction constant. The course of the conversion is followed by means of chromatography. After the conversion is completed, the reaction mixture is cooled, whereby the virtually enantiomerically pure beta-hydroxy-delta-valerolactone precipitates as crystals out of the reaction mixture, or the diluent and the esterifying agent are evaporated at the rotary evaporator and the beta-hydroxy-delta-valerolactone is separated from the residue by crystallizing or recrystallizing the beta-acyloxy-delta-valerolactone.

The process yields pure enantiomers of beta-hydroxy- and beta-acyloxy-delta-valerolactones. In so doing, it depends on the specificity of the hydrolase used, whether the (2R,3R,5S)-enantiomer or the (2S,3S,5R)-enantiomer in the racemic mixture is converted. In any event a mixture that contains one enantiomer as the hydroxy compound and the second enantiomer as the acyloxy compound is produced, since in the case that R in the general formula I denotes an acyl group, only the (2S,3S,5R)-enantiomer or only the (2R,3R,5S)-enantiomer is hydrolyzed by the hydrolase and in the case that R in the general formula I denotes hydrogen, only the (2S,3S,5R)-enantiomer or only the (2R,3R,5S)-enantiomer is acylated, whereas the other enantiomer remains unreacted in the reaction mixture. Hydroxy compounds can be readily separated from acyloxy compounds according to known methods. Following separation, both the reacted and the unreacted enantiomer can be further used. If a desired enantiomer is produced as the acylated product, it can be readily transformed into a desired enantiomerically pure beta-hydroxy-valerolactone by splitting off the acyl group, for example, through alkaline hydrolysis.

An enantiomerically pure (2S,3S,5R)-2-hexyl-3-hydroxy-5-undecyl-delta-valerolactone, separated from the racemate according to the present invention, can be used to prepare oxetanones of the formula

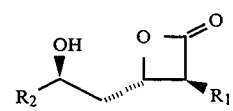

II in which $R_1$ and $R_2$ have the above mentioned meaning. Such oxetanones are used for the preparation of lipase inhibitors, especially for the preparation of N-formyl-L-leucine-(S)-1-(((2S,3S)-3-hexyl-4-oxooxetane-2-yl)-methyl)-dodecylester of the formula

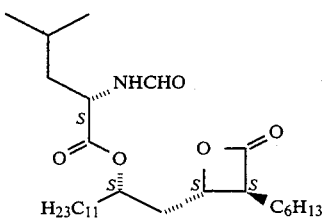

IV which is known under the trivial name tetrahydrolipstatin (THL).

A preparation of oxetanones of the formula II as well as a preparation of THL via a delta-valerolactone are described in the ZA 91/1153. The process according to the invention in a process for the preparation of an oxetanone of the formula II from a delta-valerolactone of the formula

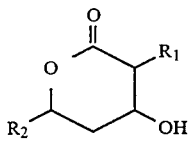

III as well as a process for the preparation of THL of the formula IV from the delta-valerolactone of the formula

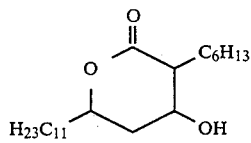

V via the oxetanone of the formula

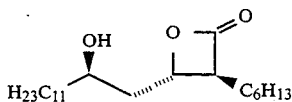

VI for providing said compounds in the enantiomerically pure form are also subject of the invention.

The resolution of racemates in the process according to the invention to prepare THL is conducted in a very early stage of the reaction sequence, whereby the unusable enantiomer has to be converted less frequently. For this reason and on account of the high reaction speed and the high selectivity, the process according to the invention represents an enlargement of the technical knowledge.

EXAMPLE 1

0.1 g of race-(2RS,3RS,5SR)-2-hexyl-3-hydroxy-5-undecyl-delta-valerolactone (0.33 mmol) (IUPAC: race-(1,u)-3-hexyl-4-hydroxy-6-undecyl-3,4,5,6-tetrahydropyran-2-one) were suspended in 2 ml of vinyl acetate and treated with 0.1 g of lipase from *Candida cylindracea*. The incubation occurred at room temperature on an agitator at 230 rpm. The course of the reaction was followed by thin layer chromatography.

After 2 hours the (2R,3R,5S)-enantiomer was totally converted into the corresponding (2R,3R,5S)-2-hexyl-3-acetoxy-5-undecyl-delta-valerolactone and the reaction had come to a standstill.

The amount of optical rotation of the acetate-alpha$_D^{20}$ - was −65°; the melting point, 93° C., which corresponds to the theoretical values.

EXAMPLE 2 was carried out like example 1, whereby 0.1 g of a lipase from Pseudomonas was used as the lipase. The results correspond to those of example 1.

EXAMPLE 3 was carried out like example 1, but using 1 g of racemate, 15 ml of vinyl acetate and 1 g of lipase from *Candida cylindracea*. After 4 hours the reaction had come to a standstill; the lipase was filtered off; the diluent was removed by distillation in a rotary evaporator and the residue was separated chromatographically (silica gel 60, eluant diisopropyl ether: n-hexane=2:1).

In so doing (2R,3R,5S)-2-hexyl-3-acetoxy-5-undecyl-delta-valerolactone was obtained with an alpha$_D^{20}$ of −65.3° and a melting point of 93° C.; and (2S,3S,5R)-2-hexyl-3-hydroxy-5-undecyl-delta-valerolactone was obtained with alpha$_D^{20}$ of +49.7° (theoretic: +48° to +50°) and a melting point of 108° C. (theoretic: 106°–108° C.).

EXAMPLE 4 was carried out like example 3, whereby 1 g of a lipase from Pseudomonas was added as the lipase. The results correspond to those of example 3.

EXAMPLE 5

300 ml of a 5% by wt. solution of race-(2RS,3RS,5SR)-2-hexyl-3-hydroxy-5-undecyl-delta-valerolactone in vinyl acetate were pumped through a module filled with 10 g of lipase from Pseudomonas at a temperature of 40° C. The course of the reaction was followed by way of gas chromatography after derivatization of the samples with N,O-bis-(trimethylsilyl)trifluoroacetamide.

After 4.75 hours the (2R,3R,5S)-enantiomer was virtually totally converted into the 3-acetoxy derivative and the reaction had come to a standstill. The lipase was subsequently washed with vinyl acetate the reaction mixture was cooled to 10° C.

In so doing, the (2S,3S,5R)-2-hexyl-3-hydroxy-5-undecyl-delta-valerolactone precipitated out as crystals in a yield of 4.5 g, which is 60% of the theoretical. Purity was more than 96%.

EXAMPLE 6 was carried out like example 3, but using 50 g of racemate, 1100 ml of vinyl acetate and 20 g of lipase from Pseudomonas.

After 5.25 hours a conversion of almost 50% was achieved.

The yield of crystalline (2S,3S,5R)-hydroxy compound was 12.5 g, which is 50% of the theoretical, with an alpha$_D^{20}$ of +49°.

EXAMPLE 7

5.0 g of race-(2RS,3SR,5SR)-2-hexyl-3-hydroxy-5undecyl-delta-valerolactone were dissolved in 102 ml of vinyl acetate at 40° C. and, after addition of 0.5 g of lipase from Alcaligenes, incubated while stirring. The course of the reaction was followed by thin layer chromatography.

After 3 hours the (2R,3R,5S)-enantiomer was totally converted into the corresponding (2R,3R,5S)-2-hexyl-3-acetoxy-5-undecyl-delta-valerolactone and the reaction had come to a standstill. After filtration the reaction solution was cooled to 10° C. and the precipitate obtained was recrystallized from the vinyl acetate. In so doing, (2S,3S,5R)-2-hexyl-3-hydroxy-5-undecyl-delta-valerolactone was obtained in a yield of 60% of the theoretical and in 97% purity.

EXAMPLE 8 was carried out like example 3, but using 300 ml of ethyl acetate, instead of vinyl acetate, with the addition of 2 equivalents of vinyl acetate based on the racemate, and with the use of 5 g of lipase from Pseudomonas.

After 30 hours the (2R,3R,5S)-enantiomer was virtually totally converted into the (2R,3R,5S)-acetoxy derivative. After cooling the reaction mixture to 10° C., the crystalline (2S,3S,5R)-2-hexyl-3-hydroxy-5-undecyl-delta-valerolactone precipitated out in a yield of 25% of the theoretical with an alpha$_D^{20}$ of 47.1° and a melting point of 106° C.

EXAMPLE 9

300 ml of a 5% by wt. solution of race-(2RS,3RS,5SR)-2-hexyl-3-hydroxy-5-undecyl-delta-valerolactone in ethyl acetate were treated with 6 equivalents of vinyl acetate, based on the racemate, and 5 g of lipase from Pseudomonas and incubated while stirring at 40° C.

After 15 hours the (2R,3R,5S)-enantiomer was almost totally converted into the (2R,3R,5S)-3-acetoxy derivative. The lipase was filtered off and the reaction mixture was cooled to 10° C.

In so doing, the (2S,3S,5R)-2-hexyl-3-hydroxy-5-undecyl-delta-valerolactone was produced as crystals in a yield of 25% with an alpha$_D^{20}$ of +48.4° and a melting point of 106° C.

EXAMPLE 10 was carried out like example 9, but using a solution of the racemate in tert.-butyl-methyl-ether, instead of ethyl acetate, of 6 equivalents of vinyl acetate, instead of 2 equivalents, and of 10 g of lipase from Pseudomonas, instead of 5 g.

After 16.75 hours the (2R,3R,5S)-enantiomer was virtually totally converted into the (2R,3R,5S)-acetoxy derivative. The yield was 2.1 g, which is 28% of the theoretical; alpha$_D^{20}$ was +48°.

EXAMPLE 11

To 300 ml of a 5% by wt. solution of race-(2RS,3RS,5SR)-2-hexyl-3-hydroxy-5-undecyl-delta-valerolactone in toluene one equivalent of acetic acid anhydride and dried, powdered KHCO$_3$ were added. The reaction mixture was pumped through a module filled with 5 g of lipase from Pseudomonas at 40° C. The course of the reaction was followed by means of thin layer chromatography. After completed conversion the reaction mixture was filtered off and extracted with diluted, aqueous NaHCO$_3$ solution. The organic phase was dried over sodium sulfate and subsequently cooled to 10° C.

In so doing, 3.5 g of (2S,3S,5R)-2-hexyl-3-hydroxy-5-undecyl-delta-valerolactone were produced, which is a yield of 46% of the theoretical, with a purity of 93%.

EXAMPLE 12

400 ml of a 2.5% by wt. solution of race-(2RS,3RS,5SR)-2-hexyl-3-hydroxy-5-undecyl-delta-valerolactone in ethyl acetate were pumped through a module filled with 5 g of lipase form Pseudomonas at a temperature of 40° C. The ethanol produced during the reaction was removed continuously through distillation.

The course of the reaction was followed by thin layer chromatography.

After complete conversion, the diluent was evaporated. The residue was recrystallized from vinyl acetate.

In so doing, 2.5 g of (2S,3S,5R)-2-hexyl-3-hydroxy-5-undecyl-delta-valerolactone were obtained, which is 50% of the theoretical, with a purity of 97%.

EXAMPLE 13 was carried out like example 12, but using 25 g of racemate, 350 ml of ethyl acetate, and 10 g of lipase from Pseudomonas at 50° C.

After complete conversion, the reaction solution was cooled, thus obtaining 10.4 g of a crystalline mixture from 73% (2S,3S,5R)-2-hexyl-3-hydroxy-5-undecyl-delta-valerolactone and 27% (2R,3R,5S)-2-hexyl-3-acetoxy-5-undecyl-delta-valerolactone. Following recrystallization from ethyl acetate, the (2S,3S,5R)-hydroxy compound was obtained with a purity of 97%.

EXAMPLE 14

1 g of race-(2RS,3RS,5SR)-2-hexyl-3-acetoxy-5-undecyl-delta-valerolactone, obtained through esterification of race-(2RS,3RS,5SR)-2-hexyl-3-hydroxy-5-undecyl-delta-valerolactone with acetic acid anhydride in the presence of dimethylaminopyridine in pyridine, was suspended in 60 ml of 0.01 molar sodium phosphate buffer, pH=7.0 and 3 ml of tetrahydrofuran. After addition of 0.5 g of lipase from Pseudomonas, the reaction mixture was incubated at 40° C., whereby the pH value was held constant through continuous addition of an aqueous, 0.1 m sodium hydroxide solution. The reaction was controlled by means of thin layer chromatography and with the aid of the consumed sodium hydroxide solution.

After about 40 hours, a conversion of 50%, based on the starting racemic product, was obtained; and the reaction had come to a standstill.

The reaction mixture was extracted with ethyl acetate and the organic phase was dried over sodium sulfate and evaporated. The residue was recrystallized from vinyl acetate.

In so doing, 0.3 g of (2R,3R,5R)-2-hexyl-3-hydroxy-5-undecyl-delta-valerolactone were obtained, which is 60% of the theoretical, with an alpha$_D^{20}$ of −48.2°. The amount of optical rotation alpha$_D^{20}$ of (2S,3S,5R)-2-hexyl-3-acetoxy-delta-valerolactone was +65°.

EXAMPLE 15

2.0 g of (5.65 mmol) of race-(2RS,3RS,5SR)-2-hexyl-3-hydroxy-5-undecyl-delta-valerolactone were dissolved in 10 ml of toluene at 40° C. and treated with 5 g of proprionic acid anhydride, 1 g of sodium hydrogen carbonate and 0.5 g of lipase from Pseudomonas. The incubation occurred at 40° C. on an agitator with 230 rpm. After 3 hours a conversion of almost 50% was obtained. Following filtering, the reaction mixture was cooled to 10° C., whereby 480 mg, which is 48% of the theoretical, crystalline, pure (2S,3S,5R)-2-hexyl-3-hydroxy-5-undecyl-delta-valerolactone were obtained.

EXAMPLE 16 was carried out like example 15, but using 0.5 g of lipase from Alcaligenes as the hydrolase.

After 2 hours a conversion of almost 50% was obtained. After filtration the reaction mixture was cooled to 10° C., whereby 0.5 g, which is 50% of the theoretical, crystalline, pure (2S,3S,5R)-2-hexyl-3-hydroxy-5-undecyl-delta-valerolactone, which was contaminated with 1.5% of the corresponding (2R,3R,5S)-propionate, were obtained.

EXAMPLE 17

2.0 g of race-(2RS,3RS,5SR)-2-hexyl-3-hydroxy-5-undecyl-delta-valerolactone (5.65 mmol) were dissolved in 10 ml of toluene at 40° C. and treated with 5 g of glycerol tributyrate and 0.5 g of lipase from Pseudomonas. The incubation occurred at 40° C. on an agitator with 230 rpm.

After 48 hours a conversion of 50% was obtained. Following filtering off of the enzyme and diluting of the reaction mixture with 10 ml of toluene, 750 mg, which is 75% of the theoretical, (2R,3R,5S)-2-hexyl-3-hydroxy-5-undecyl-delta-valerolactone, contaminated with 5% of the (2R,3R,5S)-butyrate, were obtained as crystals through cooling of the reaction mixture to 0° C.

EXAMPLE 18 was carried out like example 17, but using 0.5 g of lipase from Alcaligenes as the hydrolase.

After 48 hours a conversion of 50% was obtained. The enzyme was filtered off and the reaction mixture was cooled to 10° C., whereby 50% of the theoretical, crystalline (2S,3S,5R)-2-hexyl-3-hydroxy-5-undecyl-delta-valerolactone, which was contaminated with 1.5% of the corresponding (2R,3R,5S)-butyrate, were obtained.

EXAMPLE 19 was carried out like example 17, but using 5 g of glycerol triacetate as the esterifying agent.

After 24 hours a conversion of 50% was obtained. The enzyme was filtered off and the reaction mixture was cooled to 10° C., whereby 890 mg of a crystallizate was obtained that contained 73% of enantiomerically pure (2S,3S,5R)-2-hexyl-3-hydroxy5-undecyl-delta-valerolactone and 27% of the corresponding (2R,3R,5S)-acetate. Following recrystallization from tert.-butyl-methyl-ether, 78% of the (2S,3S,5R)-hydroxy compound obtained in the crystallizate with an $\alpha_D^{20}$ of +48° were obtained.

EXAMPLE 20 was carried out like example 19, but using 0.5 g of lipase from Alcaligenes.

After 24 hours a conversion of 50% was obtained. The enzyme was filtered off and the reaction mixture was cooled to 10° C., whereby 630 mg, which is 63% of the theoretical, of crystalline (2S,3S,5R)-2-hexyl-3-hydroxy-5-undecyl-delta-valerolactone with a purity of 93% were obtained.

EXAMPLE 21

3 g of a crystalline mixture of 77% (2S,3S,5R)-2-hexyl-3-hydroxy-5-undecyl-delta-valerolactone with 23% of (2R,3R,5S)-2-hexyl-3-acetoxy-5-undecyl-delta-valerolactone were recrystallized from tert.butyl-methyl-ether. In so doing, 1.8 g (2S,3S,5R)-2-hexyl-3-hydroxy-5-undecyl-delta-valerolactone, which is 78% based on the enantiomer used, were obtained with an $\alpha_D^{20}$ of +48°.

EXAMPLE 22

15.89 g of an equimolar crystalline mixture of (2S,3S,5R)-2-hexyl-3-hydroxy-5-undecyl-delta-valerolactone and (2R,3R,5S)-2-hexyl-3-acetoxy-5-undecyl-delta-valerolactone were recrystallized from 300 ml of toluene. In so doing, 3.5 g, which is 46% of the theoretical, (2S,3S,5R)-2-hexyl-3-hydroxy-5-undecyl-delta-valerolactone in 97% purity were obtained.

The thin layer chromatography, which is described in these examples, was conducted in diisopropyl ether:n-hexane=2:1, cer-sulfate spray reagent. The amount of optical rotation $\alpha_D^{20}$ was determined in the chloroform solution (c=1 g/100 ml). The yields, which are given in the examples, are always based on the quantity of pure enantiomer added in the starting racemic mixture.

The enantiomeric purity of (2S,3S,5R) and of 2R,3R,5S)-2-hexyl-3-acetoxy-5-undecyl-delta-valerolactone was determined by means of $^1$HNMR using tris(3-(2,2,2,-trifluoro-1-hydroxyethylidene)-d-camphorat)-europium. The amount of optical rotation $\alpha_D^{20}$ was for the (2R,3R,5S) compound −65° and for the (2S,3S,5R) compound +65°. The melting point was 93° C.

What we claim is:

1. Process to separate racemic mixtures of a compound of the formula $$\begin{array}{c} O \\ \| \\ O \diagup \diagdown R_1 \\ R_2 \diagdown \diagup OR \end{array} \quad I$$

in which R denotes hydrogen or an acyl group, and $R_1$ and $R_2$ denote independently of each other hydrogen, a straight chained or branched alkyl group having 4 to 20 C atoms, which can be interrupted by an oxygen atom in a position other than the alpha or beta position or denote an unsubstituted aralkyl group or an aralkyl group substituted by groups inert under the reaction conditions, provided that $R_1$ and $R_2$ do not simultaneously denote hydrogen, wherein the racemic mixture of a compound of formula I is introduced in a diluent and in the presence of a lipase having the abililty to catalyze stereospecifically acylation and/or deacylation of beta-hydroxy-delta valerolactones of formula I and, in the case where R in formula I denotes hydrogen in the additional presence of an esterifying agent, is left to react, whereby a reaction mixture is produced which contains an enantiomerically pure beta-hydroxy-delta-valerolactone and an enantiomerically pure beta-acyloxy-delta-valerolactone, which is then separated.

2. Process, as claimed in claim 1, wherein a compound of formula I, in which $R_1$ and $R_2$ denote independently of each other an alkyl chain having 4 to 20 C atoms, is used.

3. Process, as claimed in claim 1, wherein a compound of formula I, in-which R denotes hydrogen, is used.

4. Process, as claimed in claim 1, wherein a carboxylic acid ester of the formula $R_5COOR_6$, a vinyl alkanoate of the formula $CH_2=CH-O-COR_7$, or a carboxylic acid anhydride of the formula $R_8-CO-O-CO-R_9$, in which $R_5$, $R_6$, $R_7$, $R_8$ or $R_9$ denote an alkyl group having 1 to 6 C atoms or a glycerol triacylate is added.

5. Process, as claimed in claim 1, wherein a compound of the formula I is added, in which R is an acyl group.

6. In a process for the preparation of an enantiomerically pure oxetanone of the formula

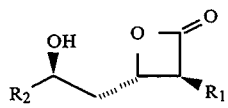   II in which $R_1$ and $R_2$ denote independently of each other hydrogen, a straight chained or branched alkyl group having 4 to 20 C-atoms, which can be interrupted by an oxygen atom in a position other than the alpha or beta position or denote an unsubstituted aralkyl group or aralkyl group substituted by inert groups under the reaction conditions, provided that $R_1$ and $R_2$ do not denote simultaneously hydrogen, from a delta-valerolactone of the formula

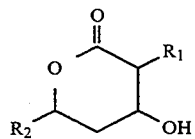   III in which $R_1$ and $R_2$ have the meaning given above, the improvement which comprises separating racemic mixtures of a compound of the formula

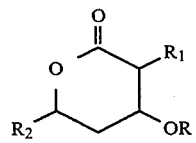   I in which R denotes hydrogen or an acyl group, and $R_1$ and $R_2$ have the meaning given above, wherein the racemic mixture of a compound of formula I is introduced in a diluent and in the presence of a hydrolase having the ability to catalyze stereospecifically acylation and/or deacylation of beta-hydroxy-delta valerolactones of formula I and, in the case that R in formula I denotes hydrogen in the additional presence of an esterifying agent, is left to react, whereby a reaction mixture is produced that contains an enantiomerically pure beta-hydroxy-delta-valerolactone and an enantiomerically pure beta-acyloxy-delta-valerolactone, which is then separated.

7. The process as claimed in claim 6 for the preparation of an enantiomerically pure oxetanone of the formula II, in which $R_1$ and $R_2$ independently of each other denote a straight chained or branched alkyl group having 4 to 20 C-atoms.

8. In the process for the preparation of N-formyl-L-lecine-(S)-1-((2S,3S)-3-hexyl-4-oxooxetane-2-yl)-methyl)dodecyl-ester of the formula

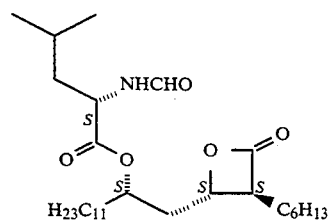   IV from the delta-valerolactone of the formula

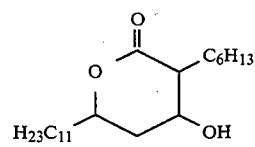   V via the oxetanone of the formula

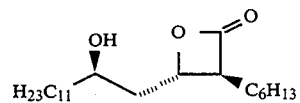   VI the improvement, wherein to separate racemic mixtures of a compound of the formula

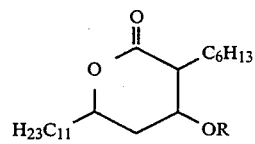   VII in which R denotes hydrogen or an acyl group, the racemic mixture of a compound of the formula VII is introduced in a diluent and in the presence of a hydrolase and, in the case that R in the formula VII denotes hydrogen in the presence of an esterifying agent, is left to react, whereby a reaction mixture is produced that contains an enantiomerically pure beta-hydroxy-delta-valerolactone and an enantiomerically pure beta-acyloxy-delta-valerolactone, which is separated by the conventional method.

9. (2S,3S,5R)-2-hexyl-3-acyloxy-5-undecyl-delta-valerolactone.

10. Enantiomerically pure compounds of the formula

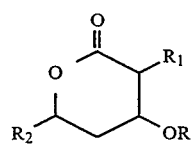   I in which R denotes an acyl group and $R_1$, and $R_2$ denote independently of each other hydrogen, a straight chained or branched alkyl group having 4 to 20 C atoms, which can be interrupted by an oxygen atom in a position other than the alpha or beta position or denote an unsubstituted aralkyl group or an aralkyl group substituted by inert groups under the reaction conditions, with the exception of (2S,3S,5R)-2-hexyl-3-benzoyloxy-5-undecyl-delta-valerolactone.

11. The process according to claim 1 wherein the reaction is performed in less than about 40 hours.

* * * * *